US007500993B2

(12) United States Patent
de la Torre et al.

(10) Patent No.: US 7,500,993 B2
(45) Date of Patent: Mar. 10, 2009

(54) VENTRAL HERNIA REPAIR METHOD

(75) Inventors: Roger A. de la Torre, Wentzville, MO (US); Matthew P. LaConte, Maryland Heights, MO (US)

(73) Assignee: Towertech Research Group, Inc., Wentzville, MO (US)

( * ) Notice: Subject to any disclaimer, the term of this patent is extended or adjusted under 35 U.S.C. 154(b) by 634 days.

(21) Appl. No.: 11/182,197

(22) Filed: Jul. 15, 2005

(65) Prior Publication Data

US 2007/0016227 A1 Jan. 18, 2007

(51) Int. Cl.
*A61F 2/02* (2006.01)
*A61B 17/10* (2006.01)
*A61B 17/08* (2006.01)

(52) U.S. Cl. ............... 623/23.72; 606/139; 606/151
(58) Field of Classification Search .......... 606/151, 606/139; 623/23.72
See application file for complete search history.

(56) References Cited

U.S. PATENT DOCUMENTS

| 5,176,692 | A | * | 1/1993 | Wilk et al. ............ 606/151 |
| 5,593,441 | A | * | 1/1997 | Lichtenstein et al. ...... 600/37 |
| 5,634,931 | A | * | 6/1997 | Kugel ................ 606/151 |
| 6,383,201 | B1 | * | 5/2002 | Dong ................. 606/151 |
| 6,596,002 | B2 | * | 7/2003 | Therin et al. .......... 606/151 |
| 6,706,048 | B2 | * | 3/2004 | de la Pena et al. ....... 606/139 |
| 2002/0065534 | A1 | | 5/2002 | Hermann et al. |
| 2004/0176785 | A1 | | 9/2004 | Hermann et al. |

OTHER PUBLICATIONS

*Operative Techniques in General Surgery*; magazine; vol. 6, Issue 3; Sep. 2004; Elsevier, Inc., Philadelphia, PA.

* cited by examiner

*Primary Examiner*—Darwin P Erezo
*Assistant Examiner*—Naveen K Singh
(74) *Attorney, Agent, or Firm*—Thompson Coburn LLP (57) ABSTRACT

A method of repairing a patient's ventral hernia involves the steps of joining the patient's left and right rectus sheaths on opposite sides of the hernia, thereby closing the hernia, and cutting through the joined sheaths thereby forming one sheath interior containing the left and right rectus muscles. Next, a piece of surgical mesh is positioned in the joined rectus sheath interior and is sutured over the area of the closed hernia to further reinforce the closure. Additionally, sutures joining the left and right rectus sheaths are reinforced with reinforcing material.

23 Claims, 11 Drawing Sheets

VENTRAL HERNIA REPAIR METHOD

BACKGROUND OF THE INVENTION (1) Field of the Invention

The present invention pertains to a method of repairing a patient's ventral hernia. More specifically, the present invention pertains to a method of repairing a ventral hernia where the patient's left and right rectus sheaths on opposite sides of the hernia are brought together and sutured, closing the hernia and forming one sheath interior containing the left and right rectus muscles. The method also involves suturing a piece of surgical mesh in the joined rectus sheath interior with the mesh positioned over the area of the closed hernia to further reinforce the closure. Additionally, the sutures joining the left and right rectus sheaths are reinforced with suture reinforcing material.

(2) Description of the Related Art

A ventral hernia typically occurs in the abdominal wall of an individual where the abdominal muscles have weakened, or where a previous surgical incision was made. Weakened abdominal muscles can result in a bulge or a tear forming in the surrounding tissue of the abdominal muscles. The inner lining of the abdomen can then push through the weakened area of the abdominal wall to form a hernia sack or bulge. Where a surgical incision was previously made in the individual's abdomen, portions of the abdominal wall that have been sutured together can separate or tear between sutures over time. This also can result in the inner lining of the abdomen pushing through the tear of the abdominal wall to form a bulge or hernia sack.

Tens of thousands of ventral hernia repairs are performed in the United States each year. The conventional surgical repair procedure, or "open" method requires that a large incision be made in the patient's abdomen exposing the area of the hernia. The hernia is closed by sutures and/or surgical mesh. The incision is then closed. Because a large incision is made in the abdomen, the "open" method of repair can result in increased post-operative pain, an extended hospital stay, and a restrictive diet.

Laparoscopic procedures have been developed for repairing ventral hernias. These procedures repair the hernia opening in the abdominal wall using small incisions in the abdomen. Laparoscopes and surgical mesh are used in a typical procedure. The mesh is inserted through a trocar and positioned at the surgical site in the abdomen to reinforce the abdominal wall in the area of the hernia. The laparoscopic method of repair can result in decreased post-operative pain and a shorter hospital stay. However, the laparoscopic procedure has also experienced some adverse affects. For example, the positioning of the surgical mesh in the abdomen can result in the mesh irritating the intestines or other abdominal contents. In addition, the surgical mesh can move in the abdomen from its original position, exposing the hernia sight and creating the potential for the development of another ventral hernia.

SUMMARY OF THE INVENTION

The present invention provides a novel procedure for repairing a patient's ventral hernia that overcomes the disadvantages associated with prior art methods.

The method of the invention employs many of the steps that are typically used in the prior art methods of repairing a ventral hernia of a patient. For example, with the patient in a supine position, an incision is made through the exterior layers of the abdomen slightly above the position of the hernia. The incision is made to expose the anterior layers of the rectus sheaths.

Incisions are then made through the anterior layers of the rectus sheaths, exposing the muscle tissues in the interiors of the sheaths.

From the incisions in the rectus sheaths, the rectus sheaths are separated from the rectus muscle tissue along lengths of the rectus sheaths on opposite sides of the hernia. The separated muscle tissue is pushed laterally outwardly from the linea albo connecting the rectus sheaths, creating interior voids in the rectus sheaths between the displaced muscle tissue and the portions of the sheaths adjacent the hernia.

The jaws of a linear cutter are then inserted through the incisions in the rectus sheaths and through the interior voids created in the sheaths. The linear cutter jaws are positioned in the sheaths on opposite sides of the hernia. In the preferred method of performing the hernia repair, the type of linear cutter used is disclosed in a copending patent application assigned to the assignee of this application. That linear cutter includes pieces of suture reinforcing material that are secured to the jaws of the cutter in positions where sutures discharged from the cutter will also pass through the pieces of the suture reinforcing material.

The jaws of the linear cutter are then closed, bringing together the two portions of the left and right rectus sheaths on opposite sides of the hernia opening. The staples of the linear cutter are discharged, forming an upper line of suture between the left and right rectus sheaths and forming a lower line of suture between the left and right rectus sheaths. Simultaneously, the cutter of the linear cutter forms an opening through the portions of the left and right rectus sheaths between the upper and lower lines of sutures. The upper and lower lines of sutures, and the cut formed by the linear cutter all form the left and right rectus sheaths as one continuous sheath in the area of the now closed hernia opening.

A piece of surgical mesh is next inserted into the joined interiors of the left and right rectus sheaths. The surgical mesh is positioned over the lower line of sutures in the area of the now closed hernia opening. The surgical mesh is positioned extending across the closed hernia opening and the lower line of sutures, beneath the left and right rectus muscles and above the left and right posterior layers of the rectus sheaths. In an improvement over prior art methods, the surgical mesh is dimensioned to extend across the posterior layers of the left and right rectus sheaths, and the laterally outer edge portions of the surgical mesh are positioned adjacent the laterally outer sides of the left and right rectus muscles. The laterally outer edge portions of the surgical mesh are sutured in place adjacent the laterally outer sides of the left and right rectus muscles. Preferably, the sutures extend through the left and right rectus sheaths, and most preferably are sutured to the exterior layers of the abdomen.

With the surgical mesh secured in place, the incisions in the left and right rectus sheaths are then closed, and the incision in the abdominal wall is then closed. This completes the hernia repair method of the invention.

BRIEF DESCRIPTION OF THE DRAWINGS

Further features of the inventive method are set forth in the following detailed description of the preferred embodiment of practicing the method, and in the drawing figures wherein.

DETAILED DESCRIPTION OF THE PREFERRED EMBODIMENT

The present invention provides a novel procedure for repairing a patient's ventral hernia that overcomes the disadvantages associated with prior art methods by providing a quality hernia repair that is easy to perform, has a low recurrence rate, has a minimal peri-operative morbidity, and is cost effective. The method is a retrorectus repair of an abdominal wall hernia that uses minimally invasive techniques and is performed with the assistance of an angled laparoscope and laparoscopic equipment.

The method begins by positioning the patient in a supine position, which is typical in abdominal surgery. In order to determine the location of the hernia opening inside the abdomen, a conventional cut-down method is used to enter the abdominal cavity at a site away from the hernia. The initial incision of the cut-down method is no more than 10-12 mm. This initial incision allows for the placement of a blunt trocar through the incision and into the peritoneal cavity. With the trocar in place, the abdomen is insufflated with 15 mm Hg pressure of carbon dioxide gas. A laparoscope is then introduced through the trocar to inspect the interior of the abdomen and the abdominal wall. If the inspection reveals any evidence of adhesions near the hernia site which are required to be lysed or dissolved, or of incarceration or confinement of tissues, which needs to be reduced, additional 5 mm trocars and laparoscopic working instruments are introduced into the abdomen under direct vision for this, purpose.

Figure 4:
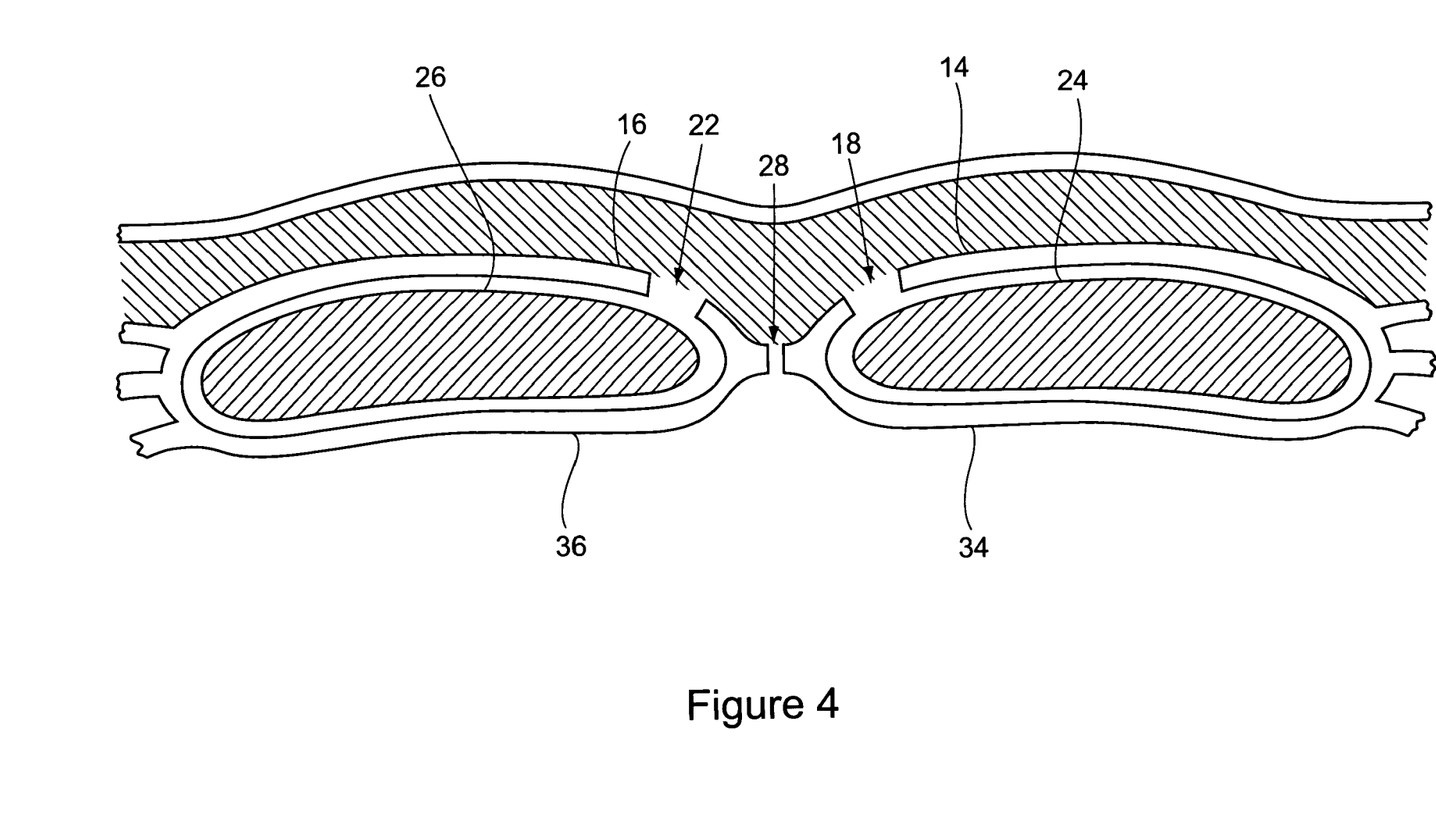
FIG. 4 is a representation of a cross-section of the left and right rectus sheaths showing the positions of the incisions through the rectus sheaths and the position of the ventral hernia to be repaired.

Once the above procedures are completed, the carbon dioxide is allowed to escape from the abdomen. Next, a transverse 4 cm incision is made across the midline of the hernia location approximately 5 cm cephalade to the hernia, or above the hernia relative to the patient's abdomen. This incision 12 is represented in FIG. 4. The incision 12 is carried down through the subcutaneous tissue of the abdomen to the level of the anterior sheaths 14, 16 of the rectus muscles.

Figure 1:
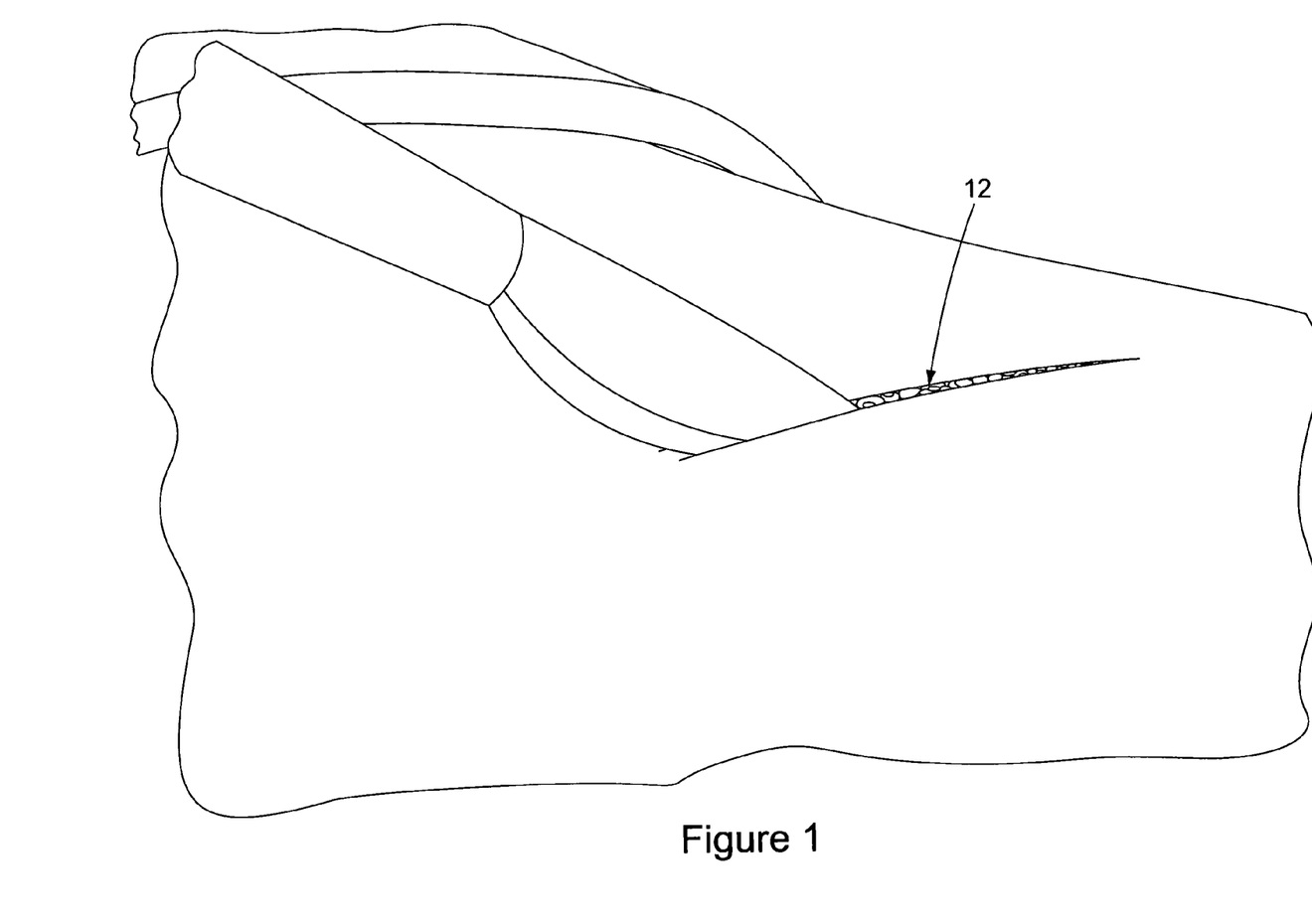
FIG. 1 is a representation of the initial incision made through the abdominal wall of the patient.
Figure 2:
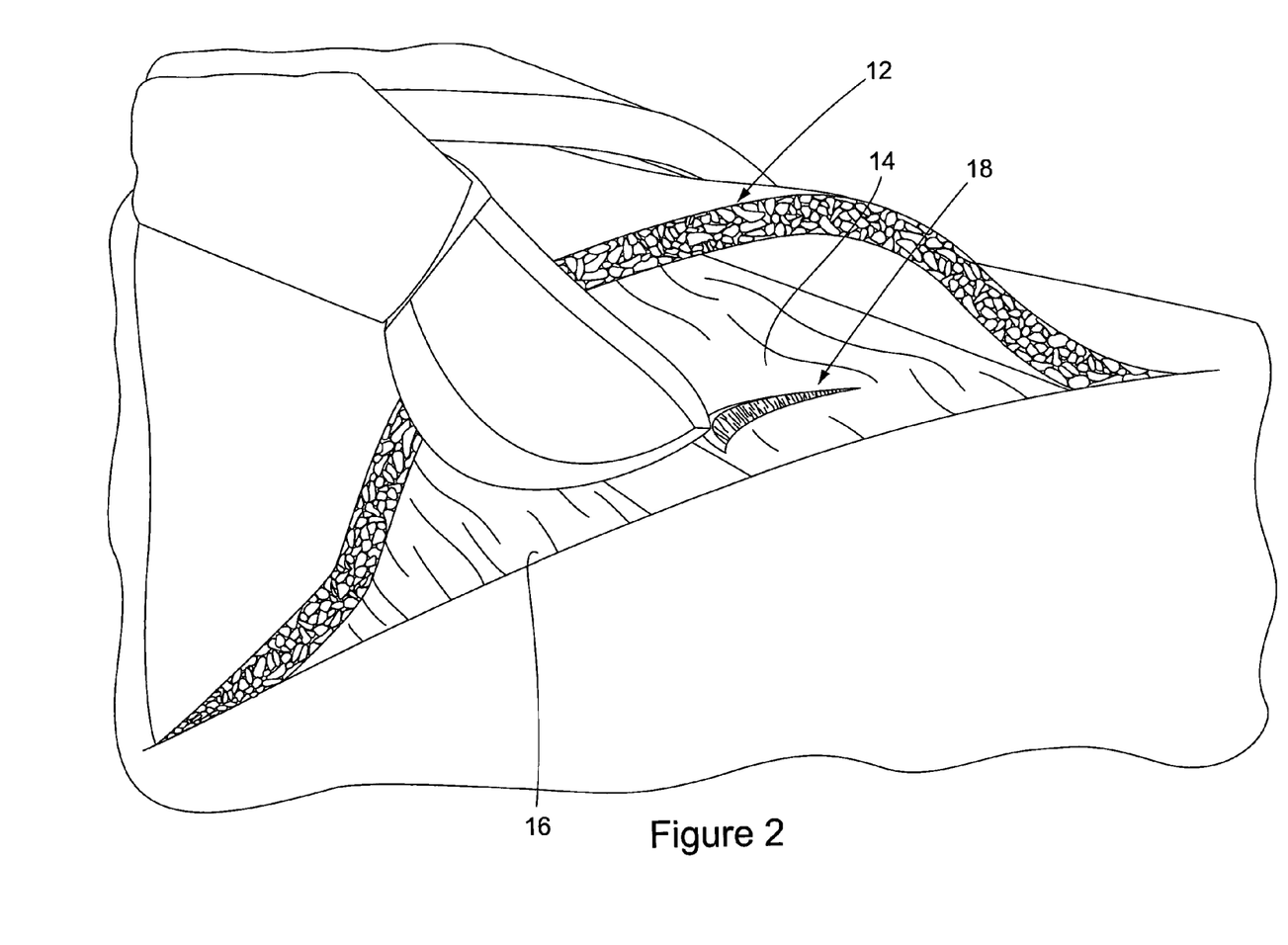
FIG. 2 is a representation of the incision made through the anterior layer of the right side rectus sheath.
Figure 3:
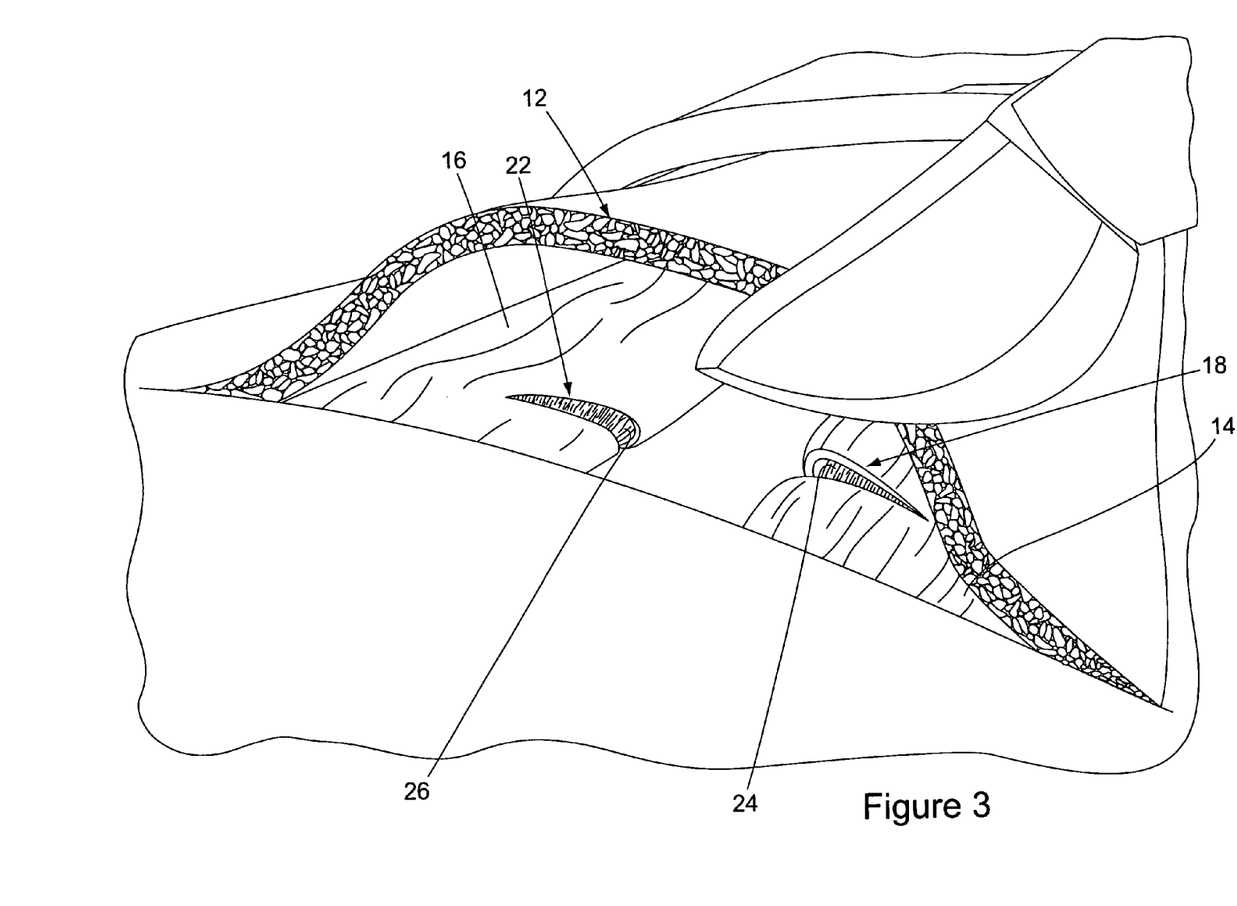
FIG. 3 is a representation of the incision made through the left side rectus sheath.

Next, as represented in FIGS. 2, 3, and 4, a pair of 1 cm longitudinal incisions 18, 22 are made in the anterior sheaths 14, 16 of both the right 24 and left 26 rectus muscles. The incisions 18, 22 are made at the medial edges of the muscles above the location of the hernia opening 28.

Figure 5:
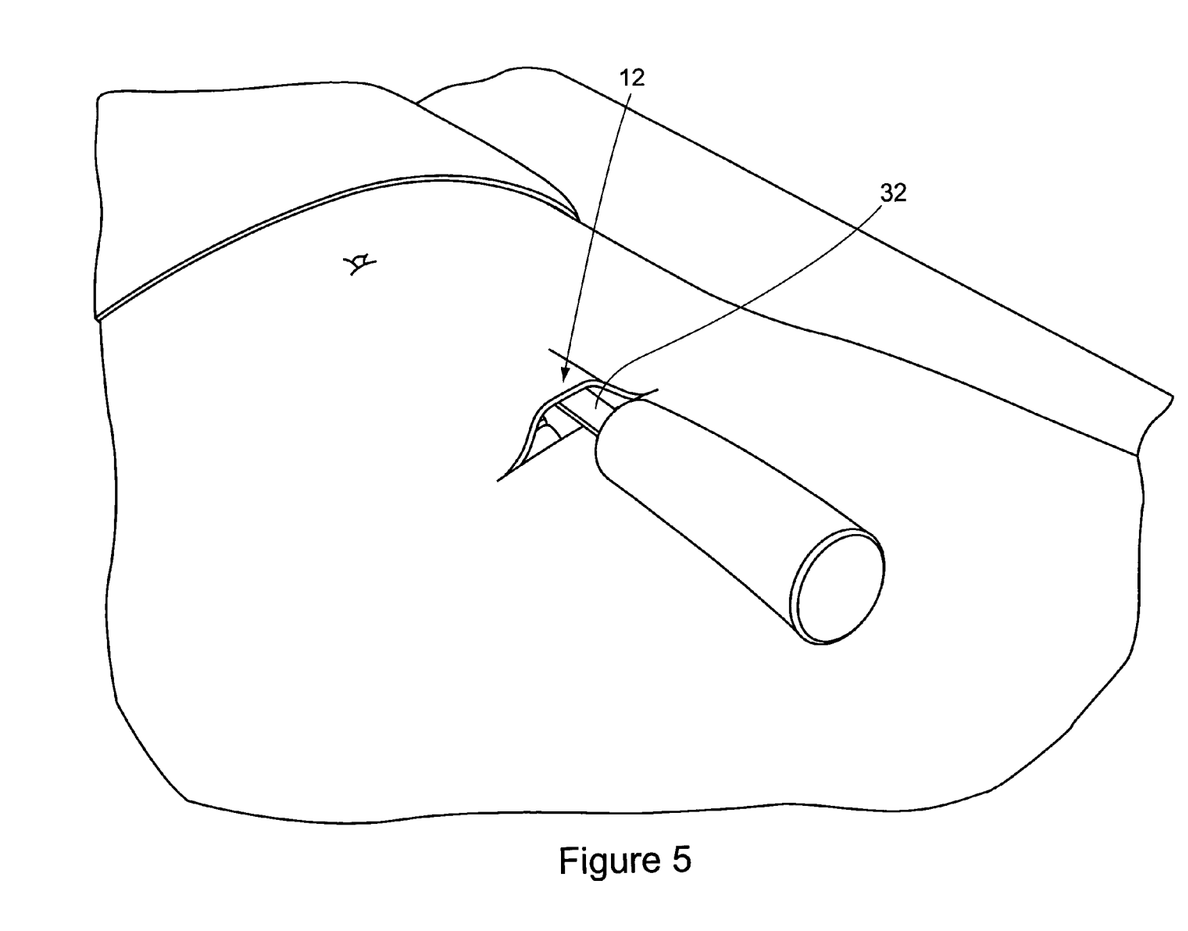
FIG. 5 is a representation of the step of creating interior voids in the left and right rectus sheaths.

The medial edges of the right rectus muscle 24 and left rectus muscle 26 are then retracted laterally outwardly away from the area of the hernia 28. As represented in FIG. 5, a long blunt clamp 32 is used to separate the right posterior sheath 34 from the right rectus muscle 24, and to separate the left posterior sheath 36 from the left rectus muscle 26 along the opposite sides of the hernia opening 28. The muscles 24, 26 are retracted laterally and held in their retracted positions by conventional Army/Navy or "S" type retractors.

Figure 6:
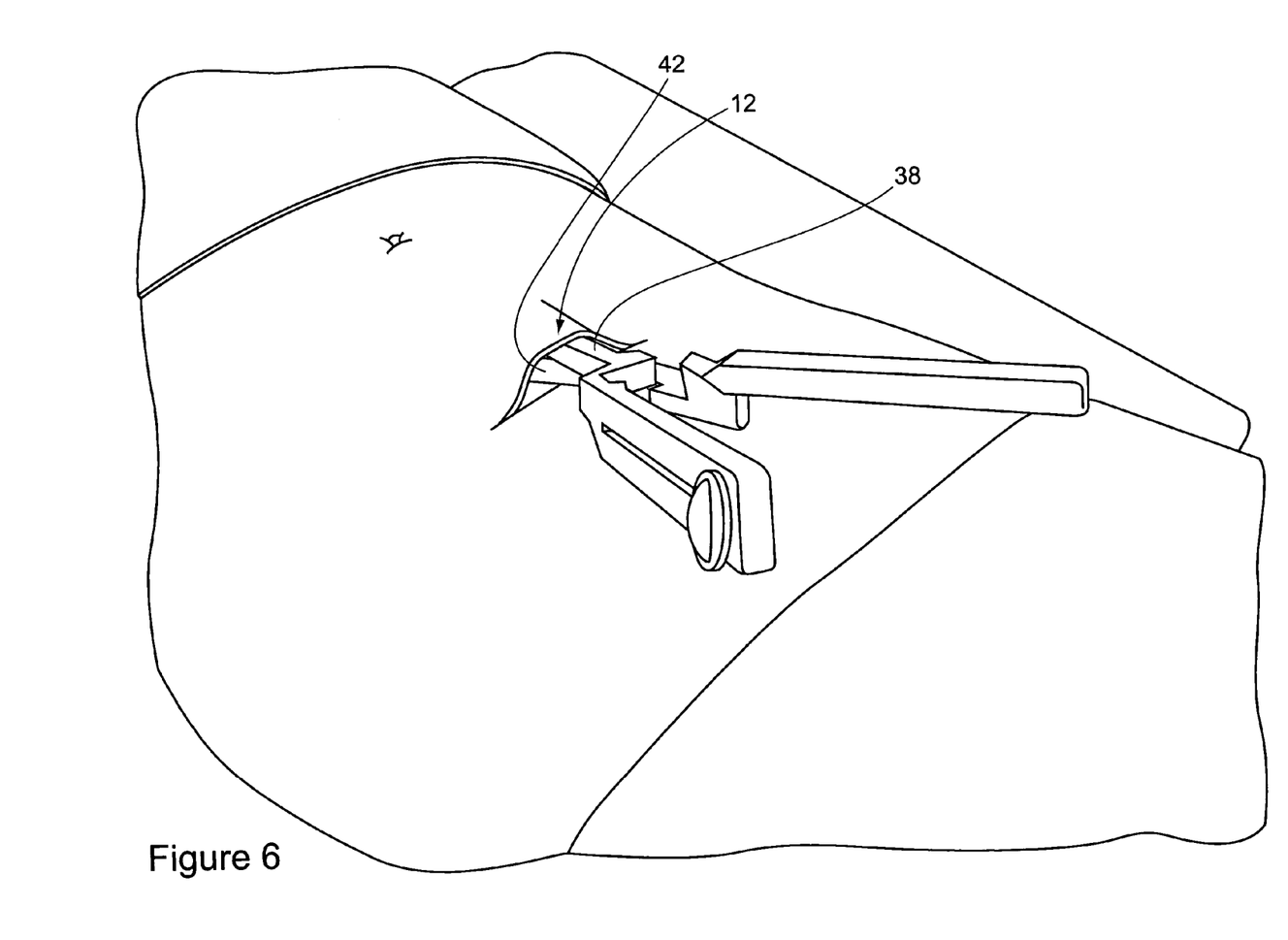
FIG. 6 is a representation of the step involving inserting the jaws of a linear cutter into the voids of the left and right rectus sheaths.
Figure 7:
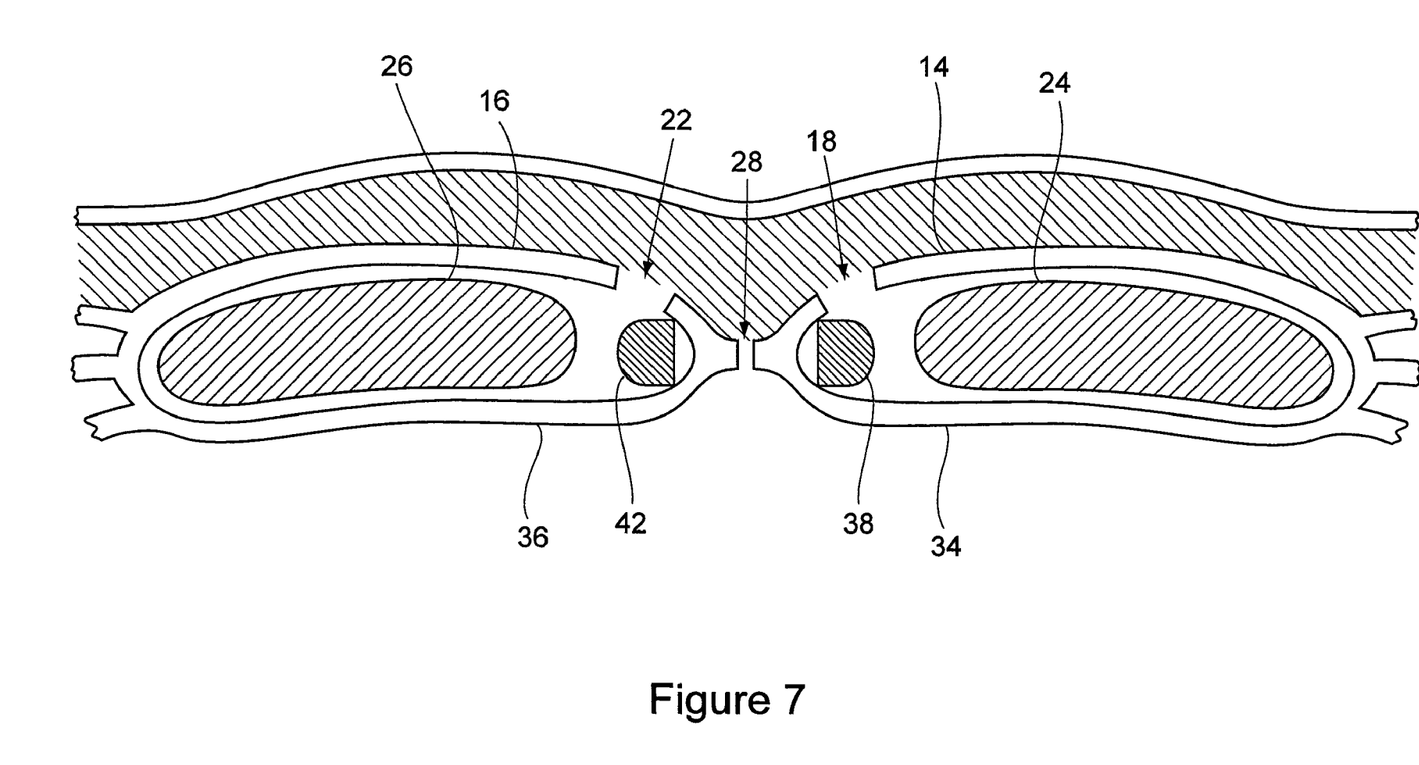
FIG. 7 is a representation of the jaws of the linear cutter in the left and right rectus sheaths.

Once the lateral retraction of the right 24 and left 26 rectus muscles in their respective sheaths is complete, a linear cutter, preferably a 100 mm linear cutter with 4.5 mm staples is separated at its hinge separating the jaws 38, 42 or limbs of the device. The type of linear cutter used in the preferred method of the invention is disclosed in a co-pending patent application assigned to the assignee of this application. That linear cutter includes pieces of suture reinforcing material that are secured to the opposing jaws 38, 42 of the cutter in positions where the sutures discharged from the cutter jaws will also pass through the pieces of reinforcing material. One of the linear cutter jaws 38 is inserted through the incision 18 in the right anterior sheath 14 and the other of the jaws 42 is inserted through the incision 22 in the left anterior sheath 16. This step of the procedure is represented in FIG. 6. The linear cutter jaws 38, 42 are inserted through the interior voids created by retracting the right 24 and left 26 rectus muscles in their respective sheaths 14, 16. The two jaws 38, 42 of the linear cutter are then again joined at their hinge connection, as represented in FIG. 6. The positions of the jaws 38, 42 opposite each other and on opposite sides of the hernia opening 28 in the right 14 and left 16 rectus sheaths is represented in FIG. 7.

Figure 8:
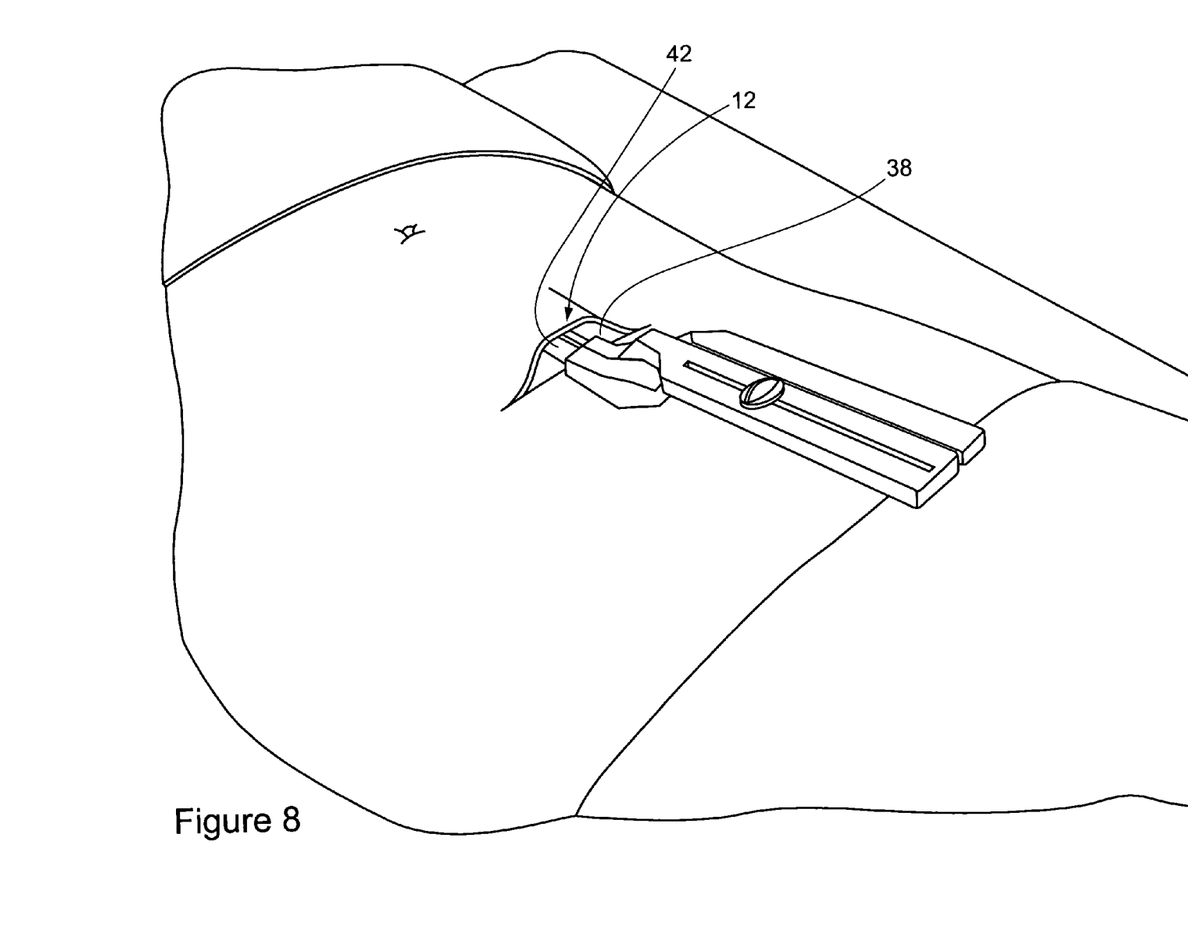
FIG. 8 is a representation of the step involving closing the jaws of the linear cutter to produce the upper and lower lines of sutures in the left and right rectus sheaths, and to cut the opening between the lines of sutures.
Figure 9:
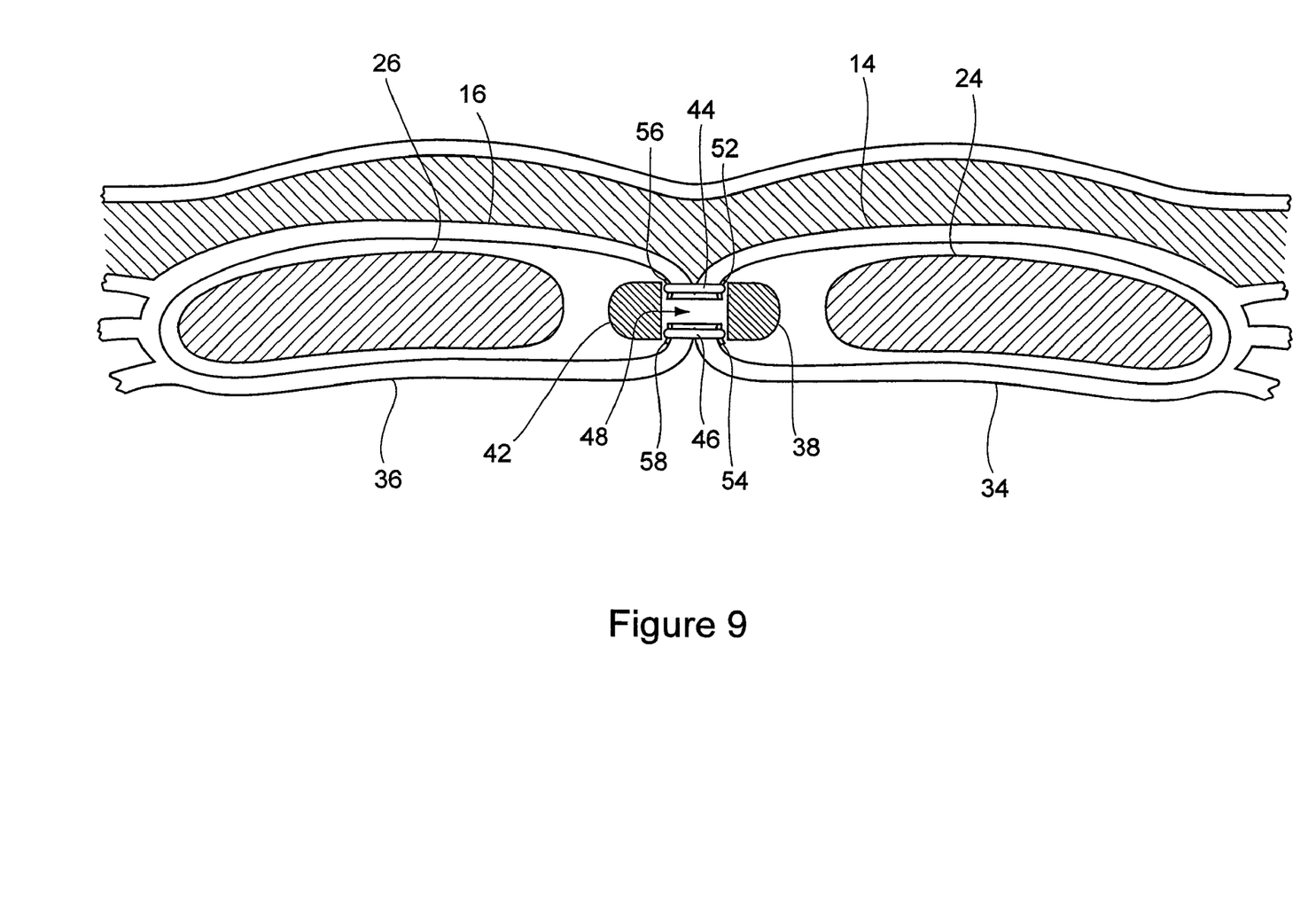
FIG. 9 is a representation of a cross-section of the left and right rectus sheaths, showing the positions of the upper and lower lines of sutures and the opening formed between the sheaths.

With the linear cutter jaws 38, 42 positioned in the interior voids in the respective right 14 and left 16 rectus sheaths, the jaws are then closed, bringing together the two portions of the right 14 and left 16 rectus sheaths on opposite sides of the hernia opening 28. This step of the procedure is represented by FIG. 8. Closing the linear cutter jaws 38, 42 is done against some tension of the right 14 and left 16 rectus sheaths, as bringing together the two portions of the sheaths will force approximation of the two rectus sheaths and collapse the hernia opening 28. Once the right 14 and left 16 rectus sheaths are closed over the hernia opening 28, the stapler is fired in a conventional manner and the staples of the linear cutter are discharged, forming an upper line of suture 44 between the right 14 and left 16 rectus sheaths, and forming a lower line of suture 46 between the right 14 and left 16 rectus sheaths. Simultaneously, the cutter of the linear cutter cuts an opening 48 through the portions of the right 14 and left 16 rectus sheaths between the upper 44 and lower 46 lines of sutures. The firing of the staples from the linear cutter jaws 38, 42 and the cut formed by the linear cutter also secures portions of suture reinforcing material 52, 54, 56, 58 on the opposite sides of the upper line of sutures 44 and on the opposite sides of the lower lines of sutures 46. The reinforcing material 52, 54, 56, 58 reinforces the sutures 44, 46 joining the portions of the right 14 and left 16 rectus sheaths above and below the cut opening 48 formed through the rectus sheaths by the linear cutter. The upper 44 and lower 46 lines of sutures, and the cut opening 48 cut by the linear cutter all form the right 14 and left 16 rectus sheaths as one continuous sheath in the area of the now closed hernia opening 28, as shown in FIG. 9. The jaws 38, 42 of the linear cutter are then removed from the incisions 18, 22 in the right 14 and left 16 rectus sheaths.

Permanent O-O suture may be used to reinforce the upper line of sutures 44 and lower line of sutures 46 in lieu of the reinforcing material 52, 54, 56, 58.

Figure 10:
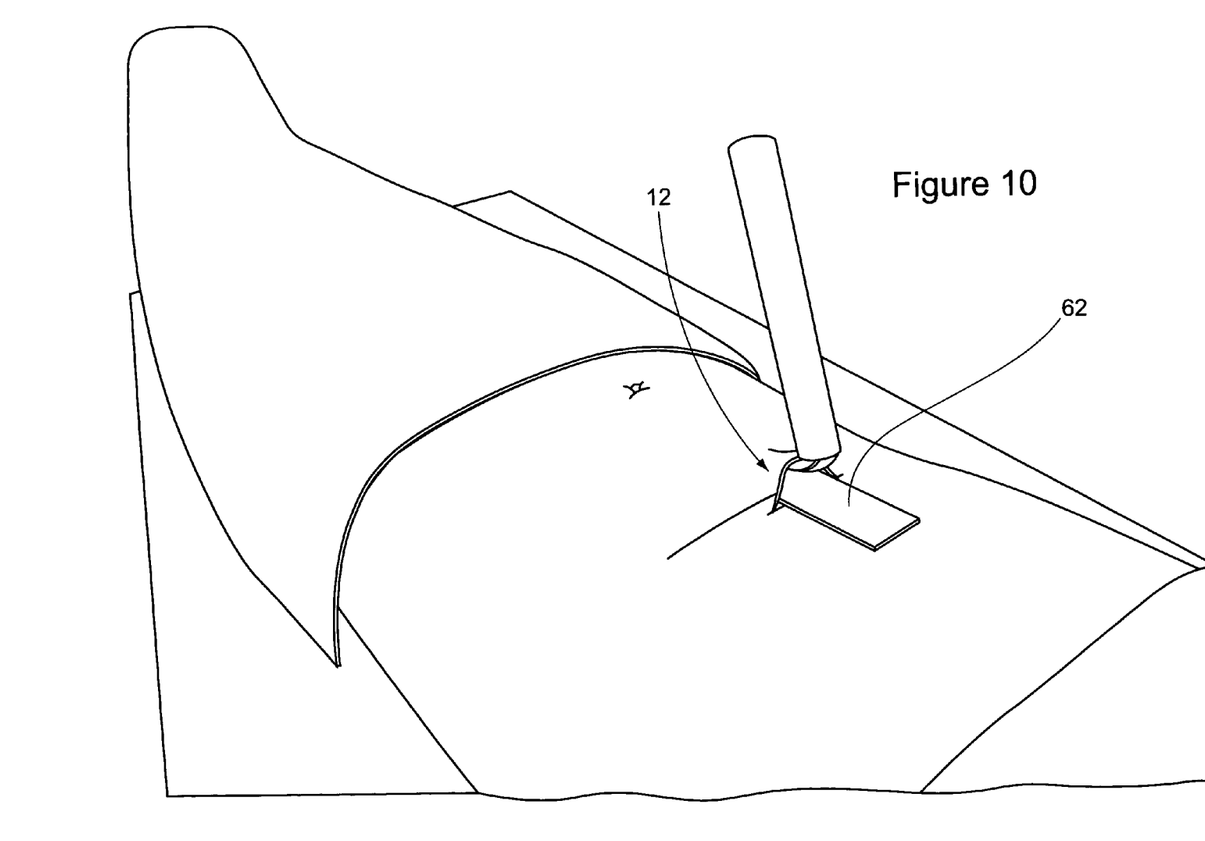
FIG. 10 is a representation of the step of inserting a piece of surgical mesh into the incision; and, FIG. 11 is a representation of the cross section through the left and right rectus sheaths showing the position of the surgical mesh at the completion of the ventral hernia repair.
Figure 11:
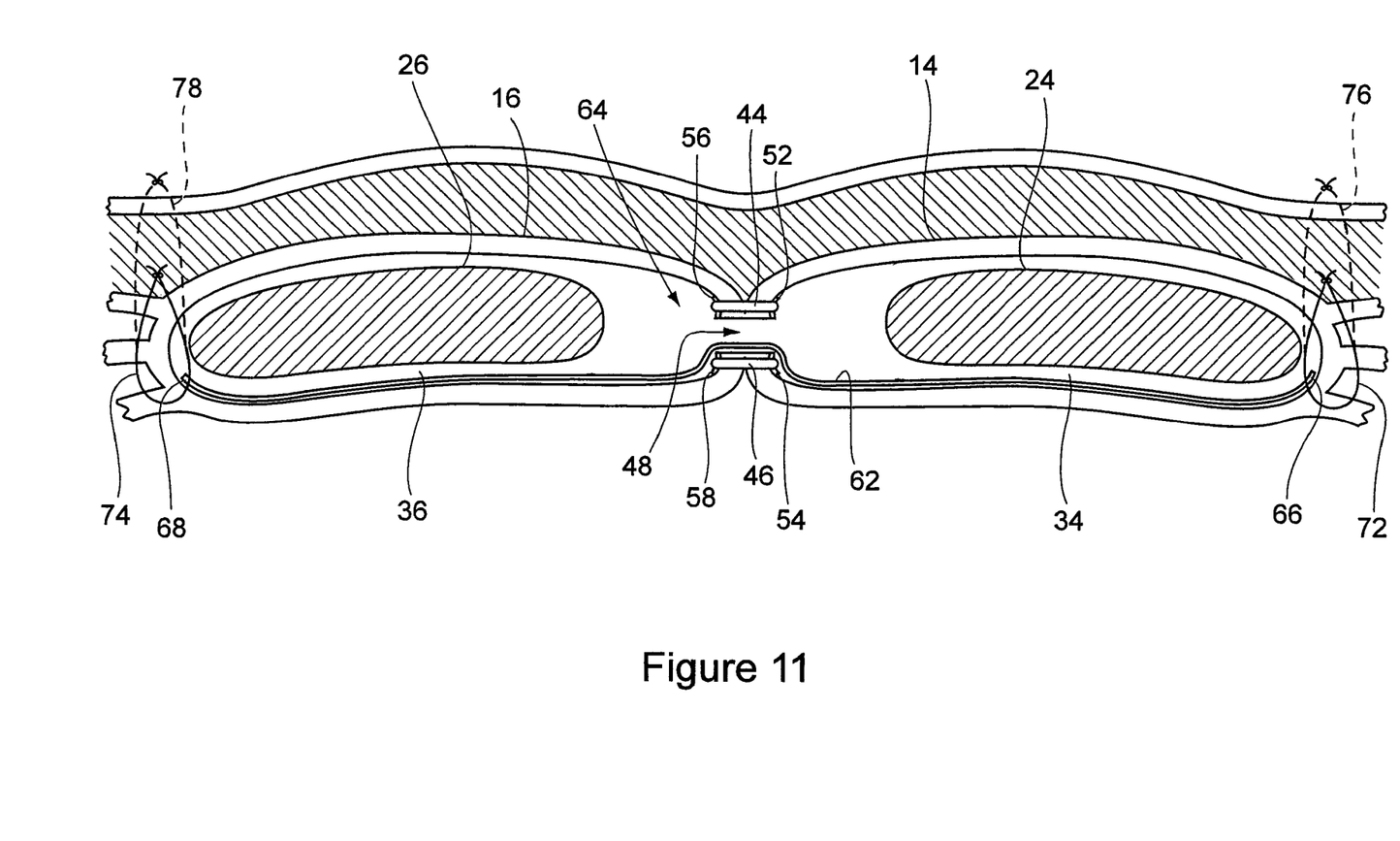

A piece of surgical mesh 62, preferably a sheet of monofilament, polypropylene mesh 62 is then cut or formed to the dimensions of the newly formed interior rectus space 64 that extends through the cut opening 48 and includes the joined interiors of the right 14 and left 16 rectus sheaths. FIG. 10 shows the insertion of the surgical mesh 62 into the joined rectus sheath interiors 64. FIG. 10 shows the insertion of the surgical mesh 62 through the abdominal incision 12 and the rectus sheath incisions 18, 22. FIG. 11 represents the positioning of the surgical mesh 62 in the joined rectus sheaths interiors 64.

As shown in FIG. 11, the surgical mesh 62 is positioned over the lower line of sutures 46 in the area of the now closed hernia opening. The surgical mesh 62 is positioned extending across the closed hernia opening and the lower line of sutures 64, beneath the right rectus muscle 24 and the left rectus muscle 26, and above the right posterior sheath 34 and the left posterior sheath 36. The surgical mesh 62 is dimensioned to extend across the right posterior sheath 34 and the left posterior sheath 36 with the laterally opposite outer edge portions 66, 68 of the surgical mesh 62 being positioned adjacent the laterally outer edges of the right rectus muscle 24 and the left rectus muscle 26. This positioning of the surgical mesh 62 is checked with the use of an angled laparoscope (not shown) with the space in the joined rectus sheath interiors 64 being held open with a lighted retractor (not shown). The mesh 62 is flattened as shown in FIG. 11, and the retractor is removed allowing the right rectus muscle and the left rectus muscle 26 to return to their normal positions in their respective rectus sheaths 14, 16. Sutures 72, 74 are then placed through the respective right side portion 66 and left side portion 68 of the surgical mesh 62, securing the mesh in place adjacent the laterally outer sides of the right 24 and left 26 rectus muscles as shown in FIG. 11. Small incisions can be made into the abdomen to position the securing sutures 72, 74 beneath the outer layers of the abdomen as shown in solid lines in FIG. 11. Alternatively, as shown in dashed lines, the securing sutures 76, 78 can extend through the right 14 and left 16 rectus sheaths as well as the right 66 and left 68 side portions of the surgical mesh 62 and through the exterior layers of the abdomen in securing the surgical mesh in place.

With the surgical mesh 62 secured in place as shown in FIG. 11, the incisions 18, 22, through the right and left rectus sheaths are closed, and the incision 12 through the abdominal wall is closed. The abdomen can then again be insufflated at low pressure to allow an internal view of the repair using the angled laparoscope. If all appears well, the trocars are removed. This completes the hernia repair method of the invention.

Although the method of the invention for repairing a hernia has been described above in repairing a patient's ventral hernia, it should be understood that the concept of the method of the invention may be employed in repairing various different types of hernias, and it should be understood that modifications and variations could be made to the method of the invention described above without departing from the intended scope of the following claims.

The invention claimed is:

1. A method of repairing a patient's ventral hernia, the method comprising the steps of:

making an incision through exterior layers of the patient's abdomen exposing the patient's left and right rectus sheaths inside the abdomen;

making incisions through anterior layers of both the left and right rectus sheaths exposing interiors of both the left and right rectus sheaths;

inserting jaws of a linear cutter through the incisions through the anterior layers of the rectus sheaths;

positioning the jaws of the linear cutter inside the interiors of the left and right rectus sheaths adjacent portions of the left and right rectus sheaths on opposite sides of the hernia;

closing the jaws of the linear cutter and thereby bringing together the portions of the left and right rectus sheaths on opposite sides of the hernia and closing the hernia;

discharging sutures from the jaws of the linear cutter and forming an upper line of sutures securing together the portions of the left and right rectus sheaths, and forming a lower line of sutures securing together the portions of the left and right rectus sheaths;

activating a cutting blade of the linear cutter and forming an opening through both the left and right rectus sheaths between the upper line of the sutures and the lower line of the sutures;

removing the jaws of the linear cutter from inside the interiors of the left and right rectus sheaths;

inserting a piece of surgical mesh through the incisions through the anterior layers of the rectus sheaths and positioning the piece of surgical mesh in the opening through both the left and right rectus sheaths between the upper line of sutures and the lower line of sutures;

suturing and securing the piece of surgical mesh in position between the upper line of sutures and the lower line of sutures;

closing the incisions through the anterior layers of the rectus sheaths; and, closing the incision through the exterior layers of the patient's abdomen.

2. The method of claim 1, further comprising:

suturing the piece of surgical mesh to both the left rectus sheath and the right rectus sheath.

3. The method of claim 1, further comprising:

positioning the piece of surgical mesh with a peripheral edge of the piece of surgical mesh spaced outwardly from the lower line of sutures.

4. The method of claim 1, further comprising:

positioning the piece of surgical mesh with a left side portion of the mesh extending into the left rectus sheath interior and being sutured to the left rectus sheath and positioning the piece of surgical mesh with a right side portion of the mesh extending into the right rectus sheath interior and being sutured to the right rectus sheath.

5. The method of claim 4, further comprising:

positioning the left side portion of the mesh between the left rectus sheath and rectus muscle tissue inside the left rectus sheath, and positioning the right side portion of the mesh between the right rectus sheath and rectus muscle tissue inside the right rectus sheath.

6. The method of claim 5, further comprising:

suturing and securing the piece of surgical mesh to the left rectus sheath and the right rectus sheath along edge portions of the piece of surgical mesh positioned at opposite sides of the rectus muscle tissue inside the left and right rectus sheaths.

7. The method of claim 6, further comprising:

suturing and securing the edge portions of the piece of surgical mesh to the exterior layers of the patient's abdomen.

8. The method of claim 1, further comprising:

positioning the piece of surgical mesh with a left side portion of the mesh extending into the left rectus sheath interior and between the left rectus sheath and rectus muscle tissue inside the left rectus sheath, and positioning the piece of surgical mesh with a right side portion of the mesh extending into the right rectus sheath interior and between the right rectus sheath and rectus muscle tissue inside the right rectus sheath.

9. The method of claim 8, further comprising:
suturing and securing the piece of surgical mesh along opposite edge portions of the surgical mesh at opposite sides of the rectus muscle tissues in the left rectus sheath and the right rectus sheath.

10. The method of claim 9, further comprising:
suturing and securing the opposite edge portions of the piece of surgical mesh to the exterior layers of the patient's abdomen.

11. The method of claim 1, further comprising:
positioning reinforcing material along the upper line of sutures and along the lower line of sutures.

12. A method of repairing a patient's ventral hernia, the method comprising the steps of:
making an incision through exterior layers of the patient's abdomen exposing the patient's left and right rectus sheaths inside the abdomen;
making incisions through anterior layers of both the left and right rectus sheaths exposing interiors of both the left and right rectus sheaths;
inserting jaws of a linear cutter through the incisions through the anterior layers of the rectus sheaths;
positioning the jaws of the linear cutter inside the interiors of the left and right rectus sheaths adjacent portions of the left and right rectus sheaths on opposite sides of the hernia;
positioning pieces of suture reinforcing material inside the interiors of the left and right rectus sheaths between the jaws of the linear cutter and the adjacent portions of the left and right rectus sheaths on opposite sides of the hernia;
closing the jaws of the linear cutter and thereby bringing together the portions of the left and right rectus sheaths on opposite sides of the hernia and closing the hernia;
discharging sutures from the jaws of the linear cutter through the pieces of suture reinforcing material and through the portions of the left and right rectus sheaths and forming an upper line of sutures through the suture reinforcing material and securing together the portions of the left and right rectus sheaths, and forming a lower line of sutures through the suture reinforcing material and securing together the portions of the left and right rectus sheaths;
activating a cutting blade of the linear cutter and forming an opening through both the left and right rectus sheaths between the upper line of sutures and the lower line of sutures;
removing the jaws of the linear cutter from inside the interiors of the left and right rectus sheaths;
closing the incisions through the anterior layers of the rectus sheath; and, closing the incision through the exterior layers of the patient's abdomen.

13. The method of claim 12, further comprising:
cutting through the pieces of suture reinforcing material with the cutting blade of the linear cutter while forming the opening through both the left and right rectus sheaths.

14. The method of claim 12, further comprising:
removably attaching the pieces of suture reinforcing material to the jaws of the linear cutter.

15. The method of claim 12, further comprising:
positioning the pieces of suture reinforcing material inside the interiors of the left and right rectus sheaths where the suture reinforcing material extends completely along the upper line of sutures and the lower line of sutures.

16. The method of claim 12, further comprising:
after discharging the sutures from the linear cutter, inserting a piece of surgical mesh through the incisions through the anterior layers of the rectus sheath and positioning the piece of surgical mesh in the opening through both the left and right rectus sheaths between the upper line of sutures and the lower line of sutures.

17. The method of claim 16, further comprising:
suturing the piece of surgical mesh to both the left rectus sheath and the right rectus sheath.

18. The method of claim 16, further comprising:
positioning the piece of surgical mesh with a left side portion of the mesh extending into the left rectus sheath interior and between the left rectus sheath and rectus muscle tissue inside the left rectus sheath, and with a right side portion of the mesh extending into the right rectus sheath interior and between the right rectus sheath and rectus muscle tissue inside the right rectus sheath.

19. The method of claim 18, further comprising:
suturing and securing the piece of surgical mesh along opposite edge portions of the surgical mesh at opposite sides of the rectus muscle tissues in the left rectus sheath and the right rectus sheath, and suturing and securing the opposite edge portions of the piece of surgical mesh to the exterior layers of the patient's abdomen.

20. A method of repairing a patient's hernia, the method comprising the steps of: making an opening through exterior layers of the patient's abdomen exposing the patient's left and right rectus sheaths; making an opening through the left and right rectus sheaths exposing interiors of the left and right rectus sheaths; bringing together upper portions of the left and right rectus sheaths on opposite sides of the hernia and lower portions of the left and right rectus sheaths on opposite sides of the hernia and thereby closing the hernia; securing together portions of the left and right rectus sheaths and the lower portions of the left and right rectus sheaths closing the hernia; making an opening through both the left and right rectus sheaths between the upper and lower secured together portions of the left and right rectus sheaths from the interior of the left and right rectus sheaths and thereby forming an opening between the interiors of the left and right rectus sheaths; then positioning a piece of surgical mesh through the opening between the interiors of the left and right rectus sheaths; positioning a piece of surgical mesh across the hernia; and, then securing the surgical mesh to the left and right rectus sheaths on opposite sides of the closed hernia.

21. The method of claim 20, further comprising:
positioning the piece of surgical mesh with a left side portion of the mesh extending into the left rectus sheath interior and between the left rectus sheath and rectus muscle tissue inside the left rectus sheath, and positioning the piece of surgical mesh with a right side portion of the mesh extending into the right rectus sheath interior and between the right rectus sheath and rectus muscle tissue inside the right rectus sheath.

22. The method of claim 21, further comprising:
suturing and securing the piece of surgical mesh along opposite edge portions of the surgical mesh at opposite sides of the rectus muscle tissues in the left rectus sheath and the right rectus sheath.

23. The method of claim 22, further comprising:
suturing and securing the opposite edge portions of the piece of surgical mesh to the exterior layers of the patient's abdomen.

* * * * *